(12) United States Patent
Virág et al.

(10) Patent No.: US 8,443,960 B2
(45) Date of Patent: May 21, 2013

(54) SYSTEM FOR HANDLING SLIDES

(75) Inventors: Tibor Virág, Budapest (HU); Béla Molnár, Budapest (HU); Ferenc Szipöcs, Budapest (HU); Ottó Németh, Szombathely (HU); Attila Biletzky, Budapest (HU); Viktor Sebestyén Varga, Budapest (HU); Attila László, Budapest (HU)

(73) Assignee: 3DHistech KFT., Budapest (HU)

( * ) Notice: Subject to any disclaimer, the term of this patent is extended or adjusted under 35 U.S.C. 154(b) by 463 days.

(21) Appl. No.: 12/663,537

(22) PCT Filed: Jun. 6, 2008

(86) PCT No.: PCT/HU2008/000065
§ 371 (c)(1),
(2), (4) Date: May 26, 2010

(87) PCT Pub. No.: WO2008/149169
PCT Pub. Date: Dec. 11, 2008

(65) Prior Publication Data
US 2010/0290868 A1 Nov. 18, 2010

(30) Foreign Application Priority Data
Jun. 8, 2007 (HU) ................................. 0700404

(51) Int. Cl.
*B65G 37/00* (2006.01)
(52) U.S. Cl.
USPC .................................. 198/346.1; 414/222.01
(58) Field of Classification Search
None
See application file for complete search history.

(56) References Cited

U.S. PATENT DOCUMENTS

| | | | | |
|---|---|---|---|---|
| 3,528,575 A | * | 9/1970 | McCaughey | 414/618 |
| 3,939,626 A | * | 2/1976 | Cioni et al. | 53/167 |
| 6,905,300 B1 | * | 6/2005 | Russum | 414/331.14 |

* cited by examiner

*Primary Examiner* — Kavel Singh
(74) *Attorney, Agent, or Firm* — Jason D. Voight

(57) ABSTRACT

A system for handling slides having a tray moving on a carriage with seats for the slides and with a tray moving mechanism, a slide loading arm, and a slide holding frame having a slide loading arm driving motor. There are outstretched Maltese crosses on the lower side of the tray of the slide feeder and a crank is arranged in the carriage, opposite to and parallel with the crosses. The slide loading arm is arranged movably and tiltably above and a supporting plate is arranged movably and tiltably below the slide holder. The slide holding frame has a lifting means for tilting the slide loading arm and the supporting plate. The lifting means is actuated by a controller arranged on the disk of the crank.

14 Claims, 3 Drawing Sheets

SYSTEM FOR HANDLING SLIDES

Figure 1:
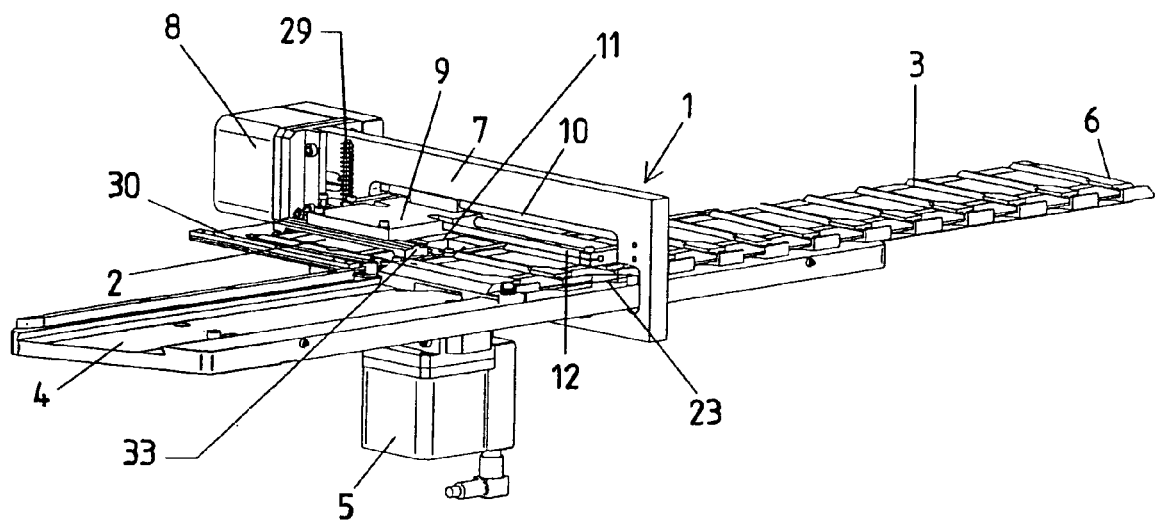

This is the National Phase of PCT/HU2008/000065, filed Jun. 6, 2008.

The invention relates to a system for handling slides, particularly a slide holder and feeding unit comprising of a tray moving on a carriage provided with seats for the slides and with a tray moving mechanism; a slide loading arm; and a slide holding frame provided with a slide loading arm driving motor.

There is a continuously growing need for complex data processing, registering and archival storage systems and for the possibility of interactive consultation of diagnostic results on the field of pathological research and medical practice.

A considerable part of the improvements relate to the adaptation of existing microscopes to the above systems. However, the structural features of microscopes applied for manual inspection do not allow much change in this respect. For the exploitation of the high velocity of the digital data processing it is inevitable to provide a slide feeding system, which is capable of following a high capacity, automated microscope operating with slide digitalization. Therefore, constructions have been developed for automated slide feeding.

The patent WO9739348 discloses a slide feeder for vertical conveying microscope slides. This transport device includes a pair of belts, the belts having a plurality of treads affixed to the outside surfaces of the belts. The belts are driven in opposite directions, so that the treads which face each other move in the same direction, either up or down. Each slide is cradled by a pair of treads, and is moved up or down, while remaining in a generally horizontal position. At the end of the path, the slides leave the system and are delivered to a storage box or a microscope table.

This slide feeder, however, does not provide for the required positioning of the slides. Furthermore, it is often not applicable for certain microscopes, due to the vertical delivering of the slides.

Patent WO0214877 provides a retrieval unit for a microarray processing device to transport a work piece such as a microscope slide before or after processing operations by the microarray processing device. The retrieval unit may include a storage unit and a lifter unit. The storage unit has a storage frame, a storage rack and a first motor. The storage rack is adapted to store microscope slides.

The storage rack is mounted to the storage frame and capable of sliding in a first plane. The lifter unit has a loader frame, a loader arm and a second motor, wherein the loader arm is capable of sliding in a second plane and accessing a selected microscope slide from the storage rack. After the microscope slide is secured to the loader arm, the microscope slide may be transported from the storage rack to a selected workstation such as an alignment mechanism. The retrieval unit is automated by having a computer control the operations of the motors.

The main advantage of this retrieval unit developed mainly for slide-matrix printing is that the errors resulted from the manual positioning may be avoided, and that time consuming manual work is not needed. However, the whole device is rather voluminous and the units of the device have sophisticated mechanical constructions optimized for the work in a printer, and therefor they cannot be satisfactorily used for other purposes.

Another slide feeding unit for microscopes is disclosed in WO2004113989. This device includes a slide magazine having a base plate, a toothed rack secured to a magazine side wall and slide guiding elements perpendicular to an open magazine side. The unit further includes a magazine moving mechanism having a magazine-receiving trough including opposite side plates. Two rotary shafts supported by the trough extend along the trough side plates. Magazine-advancing feeding gears are supported by the side plates and may mesh with the toothed magazine rack. Lifting gears, held in the side plates, have pins on which the magazine is supported when raised or lowered. Driving worm gears are rotated by the shafts and mesh with the feeding gears and the lifting gears. The unit also includes a slide feeding device having a robot arm displaceable perpendicularly to the direction of advance of the magazine for removing a slide from the magazine.

The unit according to WO2004113989 has, however rather complicated construction.

The object of the present invention is therefore to provide a slide holder and feeding unit of relatively simple construction, which is capable of feeding fresh, damp slides, without the danger of damaging them. A further object is to provide a device, which is tolerant with respect to the dimensional accuracy of the slides.

The slide holder and feeding unit according to the invention comprises a tray moving on a carriage provided with seats for the slides and with a tray moving mechanism; a slide loading arm; and a slide holding frame provided with a slide loading arm driving motor. The slide holder is provided with slide holding elements and there are outstretched Maltese crosses on the lower side of the tray of the slide feeder. A crank is arranged in the carriage, opposite to the crosses, said crank being coupled to said crosses, said slide loading arm is arranged movably and tiltable above and a supporting plate is arranged movably and tiltable below the slide holder. The supporting plate is cooperating with said slide loading arm, wherein the slide holding frame is provided with lifting means for tilting the slide loading arm and the supporting plate, said lifting means being actuated by controlling means arranged on the crank disc.

Rivets and/or a rail are protruding into the opening of the slide holder for holding the slides, wherein at least one of the rivets protruding into the opening of the slide holder is arranged on a sprig loaded arm and more than one, preferably two rivets are fixed rivets, or there is a rail on the slide holder instead of the fixed rivets.

Preferably, all the rivets have a head on their lower ends, and their diameters are growing upwards.

According to a preferred embodiment, the controlling means of the crank coupled to the crosses is a pin arranged on the mantle of the crank disc.

The lifting means of the device is a rotatable arm holding a roller cooperating with a recess of the crank, said arm being connected with an adjustable rod system, which in turn is connected at the other end with a rotatable lifting arm rotating on a pin, wherein said lifting arm is arranged between the rod system of the slide pusher and the rod system of the slide supporting plate.

The slide loading arm is connected with the tray moving motor via spindle bearing in the slide holding frame.

The slide holder is provided with a sprig loaded arm arranged on one side thereof, and there is a rivet on that arm, preferably in the middle of the arm. The diameter of the rivet is growing upwards. On the other side of the slide holder, there are rivets, preferably two rivets or a rail for positioning the slide in the slide holder.

A slide loading arm is arranged movably and tiltable above and a supporting plate is arranged movably and tiltable below the slide holder, said loading arm and said supporting plate cooperating with each other. Jump control of tray is carried out by cooperation of the rotating crank connected to the tray driving motor and the outstretched Maltese crosses on the lower side of the tray, wherein the crank is provided with an element, preferably a recess or a nose, on the peripheral side surface, opposite to the pin or pins of the crank, said element controlling the mechanism tilting the supporting plate and the slide loading arm.

Figure 2:
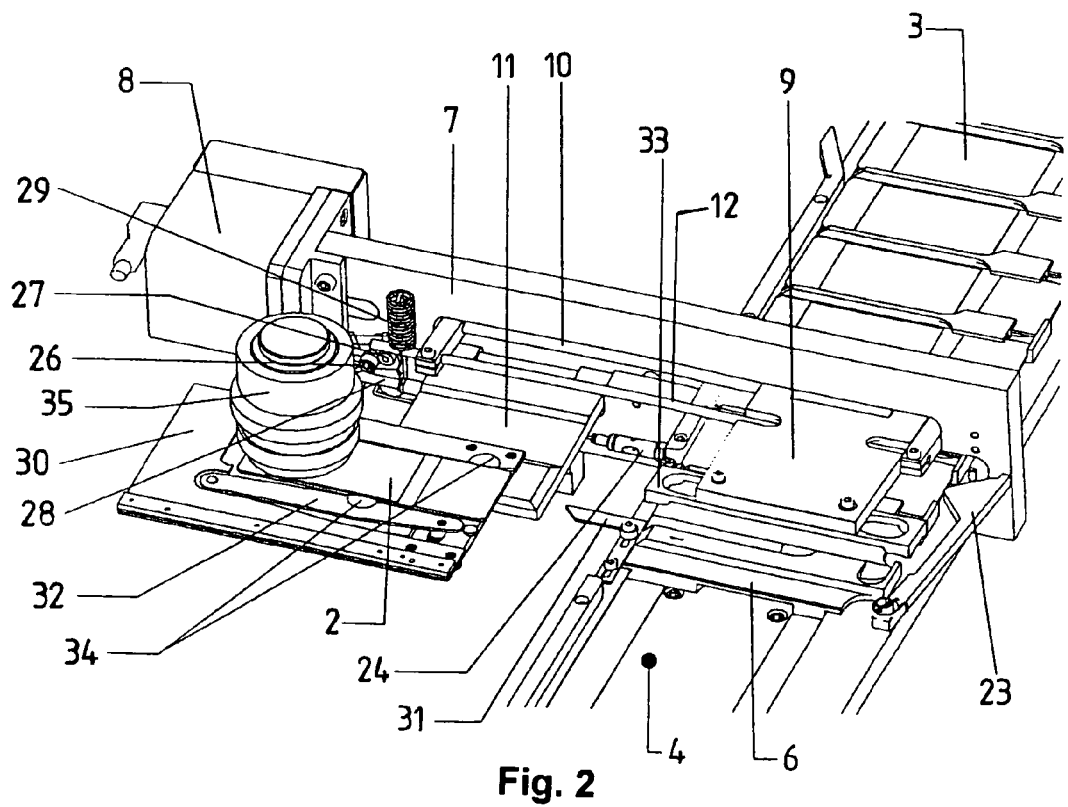
Figure 3:
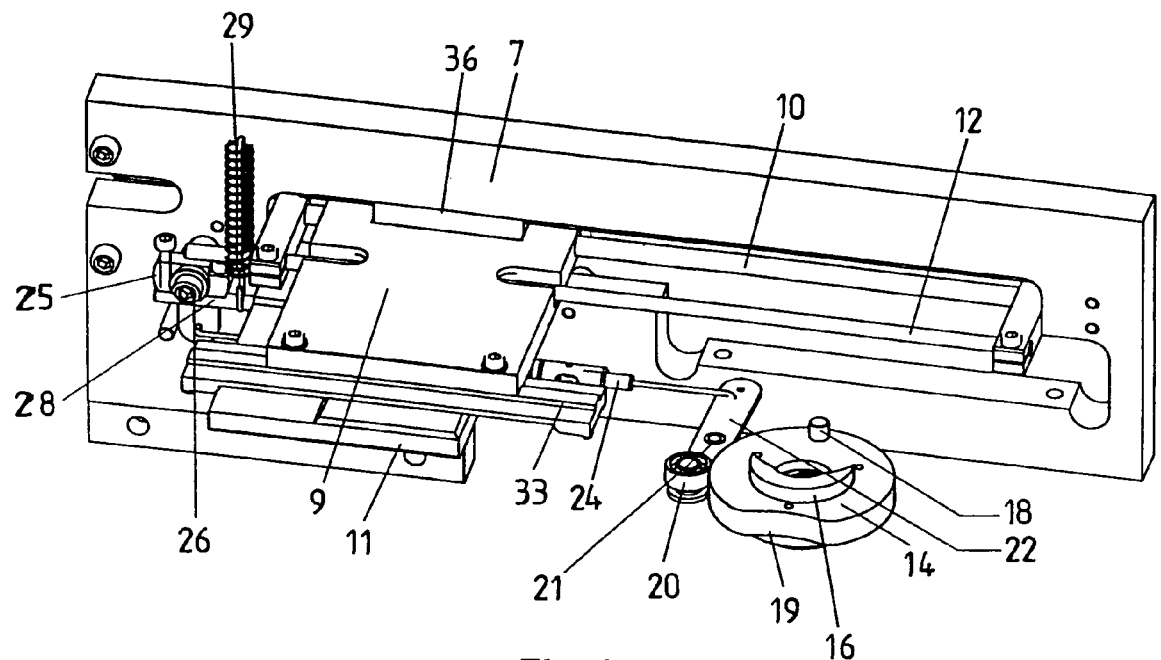
Figure 4:
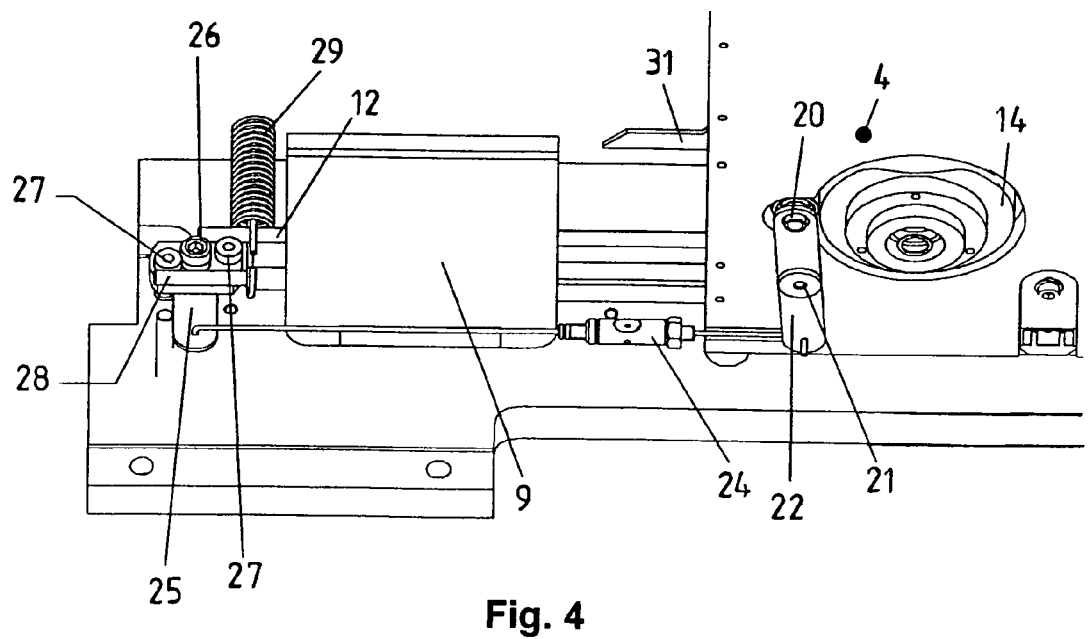
Figure 5:
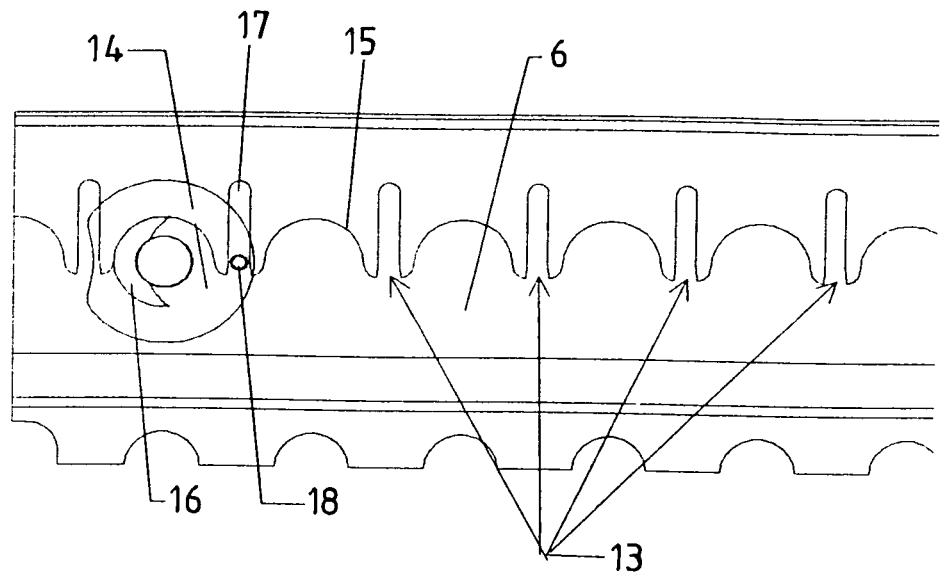
Figure 6:
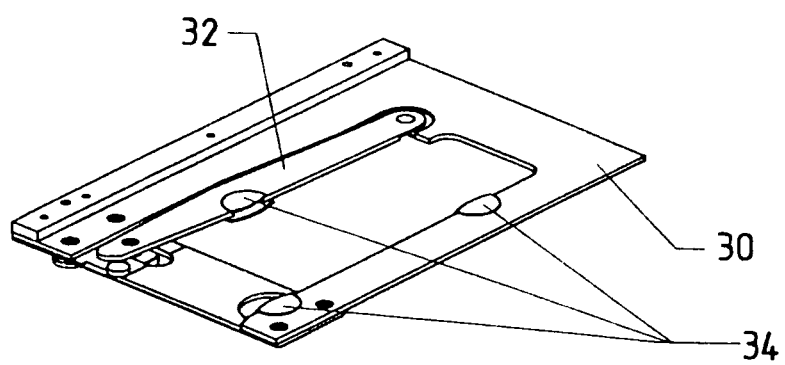
Figure 7:
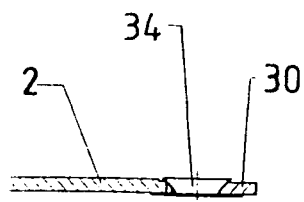

The invention will be described in detail in the following description with reference to the accompanying drawings given by way of non-limiting examples and in which FIG. 1 shows a perspective view of the slide holder and feeding unit according to the invention, FIG. 2 shows a perspective bottom view of the tray of the slide holder and feeding unit according to the invention, with an objective, FIG. 3 is a perspective top view of the lifting means of the slide holder and feeding unit according to the invention, FIG. 4 is the perspective bottom view of the lifting means for tilting the slide loading arm and the supporting plate, FIG. 5 is the bottom view of the outstretched Maltese crosses and the crank, FIG. 6 is the perspective top view of the slide holder and FIG. 7 is the cross section of a part of the slide holder and a rivet.

The slide feeder 1 in FIG. 1 comprises a tray 6 and a slide holding frame 7, said tray holding the slides 2 in seats 3 and being moved by a tray driving motor 5 in carriage 4. The slide holding frame 7 is provided with slide loading arm 9, slide loading arm driving motor 8 and spindle 10. A supporting plate 11 cooperating with the slide loading arm 9 and a tiltable rod 12 for holding the slide loading arm 9 belong to the slide holding frame 7 as well.

During operation of the device, slides 2 are arranged in the seats 3 of the tray 6. Then, tray 6 is pushed to the carriage 4 of the slide feeder 1, wherein a sensor is detecting the presence of the tray and the slide loading arm 9 is driven above the corresponding seat 3.

FIG. 5 shows that a plurality of outstretched Maltese crosses 13 are arranged on the lower side of the tray 6. Opposite to and parallel with the crosses, a crank 14 is arranged in the carriage 4 and coupled to said crosses (FIG. 3). There is a moon shaped cam 16 and a pin 18 on the upper surface of the crank 14, said cam protruding into the curved locking recesses 15 of the crosses 13, said pin protruding into the driving slots 17 of the crosses. On the side wall of crank 14, opposite to the pin 18, there is a recess 19 (FIG. 3) receiving a roll 21 running on the side wall of the crank 14 and arranged on a lever 22. This roll is cooperating with the lifting means tilting the rod 12 (FIG. 3) when carriage 4 is in locked position.

There is a feeler 23 on the upper side of the carriage 4, for detecting if there is a 2 slide in the given seat 3.

Jump control of tray 6 is carried out by rotating crank 14 with the tray driving motor.

After the slide 2 and slide holder 30 have reached the same level, recess 19 of the crank, a lifting means deflects loading arm 9 of the slide holding frame 7 (FIG. 4) and moves it towards the slide holder (30). In the meantime, bits 33 on slide loading arm 9 moving on the spindle push slide 2 into slide holder 30. At the same time, support plate 11 is tilting upwards, preventing slide 2 to fall through the opening of the slide holder 30, before being clamped therein.

FIG. 4 shows the lifting means referred to above. Here, a roll 20 arranged on one end of tiltable lever 22 is bearing up on the lateral surface of the crank. At the other end of lever 22 an adjustable rod 24 is connected, which in turn is connected at the other end thereof to another lever 25 rotating around pin 26. Lever 25 is arranged between the tiltable rod 12 holding the slide loading arm 9 and the rod 28 holding the supporting plate 11, said rods being pressed together by a spring. When recess 19 of crank 14 reaches roll 20, lifting mechanism is put in action, lever 25 as well as lever 26 is turning and, as a result, slide loading arm 9 is deflecting to slide 2 and support plate 11 is tilting upwards, holding slide 2 in position.

When slide 2 reached the correct position and sprig loaded arm 32 clamps the slide, lifting means deflects support plate 11 and tilts upwards slide loading arm 9 which is then driven to the initial position by spindle 10, and slide holder carries the slide to the objective.

FIG. 6 shows that rivets 34 and—in certain cases—a rail are protruding into the opening of slide holder 30. At least one of the rivets 34 is arranged on a spring loaded arm 32 and at least one, preferably two rivets are fixed on the frame of the slide holder. Instead of the fixed rivets, a rail may be applied.

FIG. 7 shows that rivets 34 are provided with a head on their lower end, said heads holding the slide 2, meanwhile the diameter of the rivets is growing upwards, for pressing the slides downwards and clamping them in this way.

The main advantage of the present invention is, that it makes holding and feeding the microscope slides an easy and reliable way, and is of simple construction. Due to the fact, that the slides are in horizontal position during the feeding process and do not contact any other slide, the device according to the invention can feed fresh, still wet slides as well. A further advantage of the device according to the invention is that it is not sensitive with respect to the dimensional accuracy of the slides and can, therefore accept slides with relatively high deviation in measure.

What is claimed is:

1. A slide holder and feeding unit comprising a tray moving on a carriage provided with seats for slides and with a tray moving mechanism; a slide loading arm; and a slide holding frame provided with a slide loading arm driving motor, wherein the slide holder (30) is provided with slide holding elements;

a plurality of Maltese cross elements (13) is arranged on the lower side of the tray (6) of the unit (1) and a crank (14) is arranged in the carriage (4), opposite to said cross elements (13), wherein the Maltese cross elements (13) have parallel driving slots (17) and curved locking recesses (15) arranged along a straight line and said crank (14) is coupled to said Maltese cross elements (13) by a moon-shaped cam (16) protruding into the curved locking recesses (15) and a pin protruding into said driving slots (17);

said slide loading arm (9) is arranged movably and tiltably above the slide holder (30) and a supporting plate (11) is arranged movably and tiltably below the slide holder (30), wherein said supporting plate (11) and said slide loading arm (9) are connected to each other by a lever rotating around a pin, wherein the slide holding frame (7) is provided with lifting means for tilting the slide loading arm (9) and the supporting plate (11), said lifting means being actuated mechanically by a control member arranged on the crank (14).

2. The slide holder and feeding unit according to claim 1, wherein rivets (34) are protruding into the opening of the slide holder (30) for holding the slides.

3. The slide holder and feeding unit according to claim 1, wherein a rivet (34) and a rail are protruding into the opening of the slide holder (30) for holding the slides.

4. The slide holder and feeding unit according to claim 2, wherein at least one of the rivets (34) protruding into the opening of the slide holder (30) is arranged on a spring loaded arm (32) and either more than one of the rivets (34) are fixed rivets, or there is a rail on the slide holder (30) instead of the fixed rivets.

5. The slide holder and feeding unit according to claim 2, wherein all the rivets have a head on their lower ends, and their diameters are growing upwards.

6. The slide holder and feeding unit according to claim 1, wherein the control member of the crank (14) coupled to the crosses (13) is a pin (18) arranged on the mantle of the crank disc.

7. The slide holder and feeding unit according to claim 1, wherein said lifting means is a rotatable arm (22) holding a roller (20) cooperating with a recess (19) of the crank (14), said arm (22) being connected with an adjustable rod system (24), which in turn is connected at the other end with a rotatable lifting arm (25) rotating on a pin (26), wherein said lifting arm (22) is arranged between the rod system (12) of the slide pusher (9) and the rod system (28) of the slide supporting plate (11).

8. The slide holder and feeding unit according to claim 1, wherein the slide loading arm (9) is connected with the tray moving motor (8) via spindle (10) bearing in the slide holding frame (7).

9. The slide holder and feeding unit according to claim 3, wherein all the rivets have a head on their lower ends, and their diameters are growing upwards.

10. The slide holder and feeding unit according to claim 4, wherein all the rivets have a head on their lower ends, and their diameters are growing upwards.

11. The slide holder and feeding unit according to claim 2, wherein at least one of the rivets (34) protruding into the opening of the slide holder (30) is arranged on a spring loaded arm (32) and either two of the rivets (34) are fixed rivets, or there is a rail on the slide holder (30) instead of the fixed rivets.

12. The slide holder and feeding unit according to claim 11, wherein all the rivets have a head on their lower ends, and their diameters are growing upwards.

13. The slide holder and feeding unit according to claim 2, wherein the slide loading arm (9) is connected with the tray moving motor (8) via spindle (10) bearing in the slide holding frame (7).

14. The slide holder and feeding unit according to claim 13, wherein all the rivets have a head on their lower ends, and their diameters are growing upwards.

* * * * *